US011846629B2

(12) United States Patent
Rappaport et al.

(10) Patent No.: US 11,846,629 B2
(45) Date of Patent: Dec. 19, 2023

(54) MONOMAC-1 CELLS EXPRESSING CD16 AND CD163

(71) Applicant: Temple University—Of The Commonwealth System of Higher Education, Philadelphia, PA (US)

(72) Inventors: Jay Rappaport, Somers Point, NJ (US); Sarah Vakili, Philadelphia, PA (US)

(73) Assignee: Tulane University, New Orleans, LA (US)

( * ) Notice: Subject to any disclaimer, the term of this patent is extended or adjusted under 35 U.S.C. 154(b) by 1038 days.

(21) Appl. No.: 16/334,808

(22) PCT Filed: Sep. 20, 2017

(86) PCT No.: PCT/US2017/052399
§ 371 (c)(1),
(2) Date: Mar. 20, 2019

(87) PCT Pub. No.: WO2018/057559
PCT Pub. Date: Mar. 29, 2018

(65) Prior Publication Data
US 2020/0018745 A1  Jan. 16, 2020

Related U.S. Application Data

(60) Provisional application No. 62/397,122, filed on Sep. 20, 2016.

(51) Int. Cl.
| | |
|---|---|
| *C07K 14/705* | (2006.01) |
| *C07K 14/73* | (2006.01) |
| *C07K 14/735* | (2006.01) |
| *C12N 5/0786* | (2010.01) |
| *G01N 33/50* | (2006.01) |

(52) U.S. Cl.
CPC ... *G01N 33/5047* (2013.01); *C07K 14/70514* (2013.01); *C07K 14/70535* (2013.01); *C07K 14/70596* (2013.01); *C12N 5/0645* (2013.01); *C12N 2501/052* (2013.01); *C12N 2501/22* (2013.01); *C12N 2501/24* (2013.01); *C12N 2501/25* (2013.01); *C12N 2501/30* (2013.01); *C12N 2501/39* (2013.01); *C12N 2501/999* (2013.01)

(58) Field of Classification Search
CPC ...... A61K 35/17; A61K 35/15; C12N 5/0645; C12N 2501/052; C12N 2501/22; C12N 2501/24; C12N 2501/25; C12N 2501/30
See application file for complete search history.

(56) References Cited

U.S. PATENT DOCUMENTS

| | | |
|---|---|---|
| 8,273,538 B2 | 9/2012 | Rappaport |
| 2011/0070644 A1 | 3/2011 | Huberman |
| 2016/0231322 A1 | 8/2016 | Smith |

FOREIGN PATENT DOCUMENTS

| | | |
|---|---|---|
| WO | 1997031949 | 9/1997 |
| WO | 2014172606 | 10/2014 |
| WO | 2014179751 | 11/2014 |

OTHER PUBLICATIONS

Genois et al. Mono Mac 1: a new in vitro model system to study HIV-1 infection in human cells of the mononuclear phagocyte series. J Leukoc Biol 68: 854-864, 2000.*
Hudig et al. Properties of human blood monocytes. II. Monocytes from healthy adults are highly heterogeneous within and amono individuals. Cytometry Part B 86B: 121-134, 2014.*
Jardine et al. Rapid detection of dendritic cell and monocyte disorders using CD4 as a lineage marker of the human peripheral blood antigen-presenting cell compartment. Front Immunol 4: 495, 2013 (8 total pages).*
Lambert et al. Monocytes and Macrophages in flow: an ESCCA initiative on advanced analyses of monocyte lineage using flow cytometry. Cytometry Part B 92B: 180-188, 2017 (published online Dec. 12, 2015).*
Steube et al. A model system in haematology and immunology: the human monocytic cell line mono-mac-1. Leukemia Res 21(4): 327-335, 1997.*
Tippett et al. Differential expression of CD163 on monocyte subsets in healthy and HIV-1 infected individuals. PLoS One 6(5): e19968, 2011 (11 total pages).*
Fischer-Smith et al., 2008, "CD163/CD16 Coexpression by Circulating Monocytes/Macrophages in HIV: Potential Biomarkers for HIV Infection and AIDS Progression", AIDS Res Hum Retroviruses, 24:417-421.
ISR for PCT/US17/52399 (2 pages), Dec. 12, 2017.
Written Opinion for PCT/US17/52399 (5 pages), dated Dec. 12, 2017.

* cited by examiner

*Primary Examiner* — Bridget E Bunner
(74) *Attorney, Agent, or Firm* — Riverside Law LLP

(57) ABSTRACT

The invention provides monocytes expressing CD16 and CD163 and experimental system for drug screening or evaluating drug candidates where the modulation of CD16 and CD163 is desired.

5 Claims, 15 Drawing Sheets

MONOMAC-1 CELLS EXPRESSING CD16 AND CD163

CROSS REFERENCE TO RELATED APPLICATIONS

This application is the U.S. national phase application filed under 35 U.S.C. § 371 claiming benefit to International Patent Application No. PCT/US2017/052399, filed Sep. 20, 2017, which is entitled to priority under 35 U.S.C. § 119€ to U.S. Provisional Patent Application No. 62/397,122, filed Sep. 20, 2016, the contents of which are each incorporated by reference herein in their entirety.

STATEMENT REGARDING FEDERALLY SPONSORED RESEARCH OR DEVELOPMENT

This invention was made with government support under R01 MH090910, R01 MH101010, and P01 MH105303 awarded by the National Institutes of Health. The government has certain rights in the invention.

BACKGROUND OF THE INVENTION

The status of monocyte activation appears to play a role in a variety of disease states. Monocytes and macrophages have an important role in HIV-1 infection, capable of serving as reservoirs of HIV infection, but also for their potential role in modulating adaptive immunity, thereby having the potential to contribute to the pathogenesis of AIDS. It has been demonstrated that the non-classical CD16$^+$ (FC-gammaIII receptor) monocyte is increased in frequency in HIV infection, correlating with HIV plasma viremia and inversely with CD4$^+$ T cell count in humans and rhesus macaques with HIV and SIV infection, respectively. This monocyte subset is correlated with the HIV DNA reservoirs, as well as neurocognitive impairment in HIV infection. CD16$^+$ monocytes appear also to be involved in the pathogenesis of cardiovascular disease, kidney disease, obesity, Crohn's disease and rheumatoid arthritis. In vivo, the monocyte subset that expresses CD16 and best correlates with HIV viral load also expresses CD163, a hemoglobin/haptoglobin receptor. This monocyte subset likely represents a precursor to inflammatory tissue macrophages implicated in these diseases as well as in certain cancers where tumor macrophages expressing CD16 and CD163 appear to play a role in tumor progression.

MonoMac-1 is a human cell line, which possess some properties of blood monocytes and it can be used as an in vitro model system for studying the monocytic, biochemical, immunological, and genetic functions of monocyte/macrophage lineage. Macrophages play a critical role in various pathological conditions such as infection, (chronic) inflammation and atherosclerosis. Although macrophages originate from a common myeloid progenitor cell in the bone marrow, mature macrophages constitute a very heterogeneous. Their functional heterogeneity is due to phenotypically diversity between macrophages and ranges from phagocytosis of microorganisms or particles to regulation of local immune response by production of cytokines and other types of mediators. Depending on their tissue site and activation status, a range of macrophages from resting resident (e.g., alveolar macrophage) to fully activated inflammatory macrophages can be found. To exercise their function, macrophages express various receptors such as scavenger receptors, adhesion molecules, and receptors for soluble mediators such as cytokines, chemokines, prostaglandins, and growth factors (Fischer-Smith et al., AIDS Res Hum Retroviruses, 2008, 24:417-421). The expression of different receptors varies depending on the tissue localization and activation status of the macrophages. Studies on the working mechanisms and the description of the intracellular signal pathway in macrophages have been hampered by the fact that often more than one of these receptors is involved in the binding of one ligand.

While it is known that (macrophage colony-stimulating factor) MCSF and dexamethasone are inducers of CD16 expression in vivo and in vitro in primary tissue culture models, there are no cell lines where the induction of CD16 expression can be studied and drug candidates evaluated. In view of the inherent difficulty in working with primary cells as well as donor variation, cell lines may be preferable to primary cells for their consistency. There is thus a need in the art for cell lines where CD16 expression can be studied and drug candidates evaluated. The present invention addresses this unmet need in the art.

SUMMARY OF THE INVENTION

In one embodiment, the invention relates to a monocyte, wherein the monocyte expresses at least one protein selected from the group consisting of CD16, CD163, CD4 and a combination thereof. In one embodiment, the monocyte is cultured in the presence of at least one of phorbol-12-myristate-13-acetate (PMA), lipopolysaccharide (LPS), macrophage colony-stimulating factor (MCSF), dexamethasone (DEX), TNFα and IFNγ. In one embodiment, the monocyte is a MonoMac-1 cell.

In one embodiment, the invention relates to a method of culturing monocyte cells to induce the expression of a protein selected from the group consisting of CD16, CD163, CD4 and a combination thereof.

In one embodiment, the method comprises culturing a monocyte cell in the presence of one or more of PMA, LPS, MCSF, DEX, TNFα and IFNγ.

In one embodiment, the method comprises culturing a monocyte cell line in the presence of one or more of PMA and LPS. In one embodiment, the monocyte cells are cultured for at least three days. In one embodiment, the method further comprises culturing the monocyte cell line in the presence of at least one of MCSF, DEX, TNFα and IFNγ.

In one embodiment, the method comprises culturing the monocytes in the presence of one or more of PMA and LPS followed by culturing the monocytes in the presence of at least one of MCSF, DEX, TNFα and IFNγ. In one embodiment, the monocyte cells are cultured for at least three days in the presence of PMA and LPS prior to the addition of MCSF, DEX, TNFα and IFNγ.

In one embodiment, the invention relates to a method of screening for a compound that modulates the level or activity of at least one protein selected from the group consisting of CD16, CD163, CD4 and a combination thereof, the method comprising the steps of contacting a monocyte, wherein the monocyte expresses at least one protein selected from the group consisting of CD16, CD163, CD4 and a combination thereof, with a test compound and evaluating the level or activity of at least one protein selected from the group consisting of CD16, CD163, CD4 and a combination thereof.

In one embodiment, the invention relates to a compound that modulates the level or activity of at least one protein selected from the group consisting of CD16, CD163, CD4 identified from the screening assay. In one embodiment, the compound is selected from the group consisting of a chemical compound, a protein, a peptide, a peptidomemetic, an antibody, a nucleic acid, an antisense nucleic acid, an siRNA, a miRNA, a shRNA, a ribozyme, an allosteric modulator, and a small molecule chemical compound.

In one embodiment, the compound inhibits CD16.

In one embodiment, the compound inhibits CD163.

In one embodiment, the invention relates to a composition comprising a compound that modulates the level or activity of at least one protein selected from the group consisting of CD16, CD163, CD4 identified from the screening assay. In one embodiment, the composition is a pharmaceutical composition.

In one embodiment, the invention relates to a method of treating or preventing a disease or disorder comprising administering a composition comprising a compound that modulates the level or activity of at least one protein selected from the group consisting of CD16, CD163, CD4 identified from the screening assay to a subject in need thereof. In one embodiment, the disease or disorder is associated with inflammation and immune activation.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A depicts the percentage of $CD163^+$ monocytes. FIG. 1B depicts the percentage of $CD16^+$ monocytes. FIG. 1C depicts the percentage of $CD4^+$ monocytes.

FIG. 2, comprising FIG. 2A depicts the frequency of $CD16^+$ $CD163^+$ monocytes after 3 days of PMA treatment. FIG. 2B depicts the frequency of $CD16^+$ $CD163^+$ monocytes after 3 days of PMA and LPS treatment. FIG. 2C depicts the frequency of $CD16^+$ $CD163^+$ monocytes after 3 days of PMA treatment followed by 4 days of DEX and MCSF treatment. FIG. 2D depicts the frequency of $CD16^+$ $CD163^+$ monocytes after 3 days of PMA and LPS treatment followed by 4 days of DEX and MCSF treatment.

FIG. 3, comprising FIG. 3A depicts a dot plot showing expression of $CD16^+$ and $CD163^+$ in monocytes after 3 days of PMA treatment. FIG. 3B depicts a dot plot showing expression of $CD16^+$ and $CD163^+$ in monocytes after 3 days of PMA and LPS treatment. FIG. 3C depicts a dot plot showing expression of $CD16^+$ and $CD163^+$ in monocytes after 3 days of PMA treatment followed by 4 days of DEX and MCSF treatment. FIG. 3D depicts a dot plot showing expression of $CD16^+$ and $CD163^+$ in monocytes after 3 days of PMA and LPS treatment followed by 4 days of DEX and MCSF treatment.

FIG. 4, comprising FIG. 4A depicts the percentage of $CD16^+$ monocytes. FIG. 4B depicts the percentage of $CD4^+$ monocytes. FIG. 4C depicts the percentage of $CD163^+$ monocytes.

FIG. 5, comprising FIG. 5A depicts the differentiation of MonoMac-1 cells without any treatment. FIG. 5B depicts the differentiation of MonoMac-1 cells after 3 days of PMA and LPS treatment.

FIG. 5C depicts the differentiation of Monomac-1 cells after 3 days of PMA and LPS treatment followed by 4 days of DEX and MCSF treatment.

FIG. 6, comprising FIG. 6A depicts exemplary results demonstrating that TNF and IFN increase the expression of $CD163^+$ significantly. FIG. 6B depicts exemplary results demonstrating that TNF and IFN increase the expression of $CD16^+$ significantly. (*$p\leq0.05$ and $p\leq0.01$, *$p\leq0.001$, ****$p\leq0.0001$)

FIG. 7, comprising FIG. 7A depicts the results of exemplary experiments demonstrating that adding IFN to the combination of PMA, LPS, MCSF and DEX decreased the tryptophan concentration. FIG. 7B depicts the results of exemplary experiments demonstrating that adding IFN to the combination of PMA, LPS, MCSF and DEX increased the kynurenine concentration. FIG. 7C depicts the results of exemplary experiments demonstrating that the KT ratio goes up. (*$p\leq0.05$ and $p\leq0.01$, *$p\leq0.001$, ****$p\leq0.0001$).

DETAILED DESCRIPTION

Figures 1A, 1B:
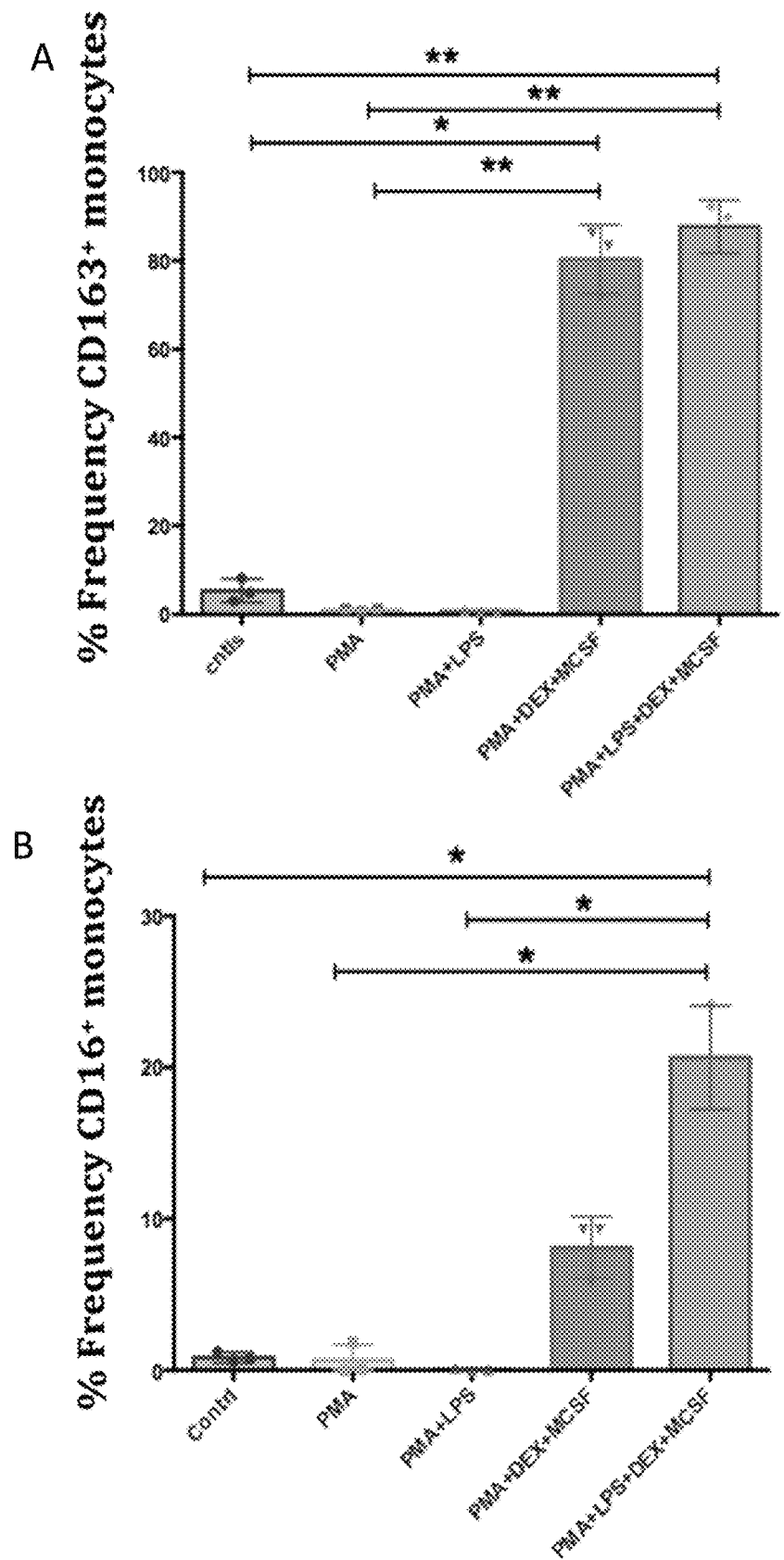
FIG. 1A through FIG. 1C, depicts experimental results demonstrating that the combination of MCSF, Dexamethasone (DEX), phorbol-12-myristate-13-acetate (PMA) and lipopolysaccharide (LPS) increase the frequency of expression of $CD16^+$ $CD163^+$ $CD4^+$ human monocytes in vitro. For FIG. 1A through FIG. 1C, MONOMAC-1 cells were treated with PMA alone or PMA and LPS for 3 days followed by addition of DEX+MCSF for 4 days. The direct influence of adding DEX and MCSF on the expression of CD163, CD16 and CD4 was studied by incubation monocytes for 7 days.

The present invention relates to the discovery of an assay where CD16, a marker involved in the pathogenesis of inflammatory diseases, HIV, and aging can be induced. Accordingly, one aspect of the invention related to a method of identifying novel compounds which target CD16, and their use as a therapeutic. In one embodiment, the invention includes compositions that target CD16.

In one embodiment, the invention includes the use of the assay to screen for agents that target CD16. In one embodiment, the invention includes the use of the assay to screen for agents that target CD163. In one embodiment, the invention includes agents that are identified from the screen. In one embodiment, the invention provides a system for drug screening or evaluating drug candidates where the modulation of CD16 and CD163 is desired.

In one embodiment, the invention includes a method of culturing MonoMac-1 (monocytes) cells to induce expression of one or more of $CD16^+$, $CD163^+$ and $CD4^+$.

In one embodiment, the invention provides a system or method to induce CD16 expression in a cell type for screening and identification of drug candidates. The drug candidates are useful for treatment of diseases where the etiology involves the expansion of the $CD16^+$ monocytes subset or the accumulation of $CD163^+/CD16^+$ tissue macrophages.

In one embodiment, the invention provides new inhibitors of CD16 monocyte differentiation that can be used for treatment of inflammatory diseases and evaluation of candidate molecules for this purpose.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, the term "autologous" is meant to refer to any material originating from the same individual to which it is later to be re-introduced into the individual.

"Allogeneic" refers to a graft derived from a different animal of the same species.

"Xenogeneic" refers to a graft derived from an animal of a different species.

The term "derived from" refers to being generated, synthesized, or originating from a particular source, such that the derived matter is related to the source. The derived matter does not need to be identical to the particular source.

In one embodiment, a cell is derived from a progenitor cell. In another embodiment, a cell is derived from a graft from a subject.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of monocyte cells. In one embodiment, the monocyte cells that are expanded ex vivo increase in number relative to the number originally present in the culture. In another embodiment, the monocyte cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Parenteral" administration of an immunogenic composition includes, e.g., subcutaneous (s.c.), intravenous (i.v.), intramuscular (i.m.), or intrasternal injection, or infusion techniques.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention includes methods and compositions for generating a monocyte cell having an increased level of expression or activity of at least one protein selected from CD16, CD163, CD4 or a combination thereof. In some embodiments, the invention includes a method for generating the monocyte cell. Other embodiments include a monocyte cell, a population of monocyte cells, generated using the methods of the invention. In one embodiment, the invention provides a cell, or a population of cells derived from a monocyte cell generated using the methods of the invention. In one embodiment, the invention includes a method for screening for compounds that affect the level of expression or activity of at least one protein selected from CD16, CD163, CD4 using the monocyte cells, or cells derived therefrom, of the invention.

Monocyte Cells

The present invention includes a monocyte cell with an increased level of expression of at least one protein selected from CD16, CD163, CD4. The present invention includes a monocyte cell with an increased KT ratio.

In one embodiment, the monocyte cell of the invention comprises a monocyte cell that has been expanded in the presence of one or more of phorbol-12-myristate-13-acetate (PMA), lipopolysaccharide (LPS), macrophage colony-stimulating factor (MCSF), dexamethasone (DEX), TNFα and IFNγ.

In one embodiment, the monocyte cell of the invention has an increased level of expression of CD16 that increased by at least 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3.0 fold, 3.5 fold, 4.0 fold, 5.0 fold, 6.0 fold, 7.0 fold, 8.0 fold, 9.0 fold, 10 fold, 15 fold, 20 fold, 25 fold, 30 fold, 35 fold, 40 fold, 45 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold or greater, and any and all whole or partial integers therebetween, in a monocyte cell cultured in the presence of one or more of PMA, LPS, MCSF, DEX, TNFα and IFNγ over the expression level of a monocyte cell that is not proliferated in the monocyte proliferating culture medium of the present invention.

In one embodiment, the monocyte cell of the invention has an increased level of expression of CD163 that increased by at least 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3.0 fold, 3.5 fold, 4.0 fold, 5.0 fold, 6.0 fold, 7.0 fold, 8.0 fold, 9.0 fold, 10 fold, 15 fold, 20 fold, 25 fold, 30 fold, 35 fold, 40 fold, 45 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold or greater, and any and all whole or partial integers therebetween, in a monocyte cell cultured in the presence of one or more of PMA, LPS, MCSF, DEX, TNFα and IFNγ over the expression level of a monocyte cell that is not proliferated in the monocyte proliferating culture medium of the present invention.

Sources of Monocyte Cells

Prior to expansion, a source of monocyte cells may be obtained from a subject. Non-limiting examples of subjects include humans, dogs, cats, mice, rats, and transgenic species thereof. Preferably, the subject is a human. Monocyte cells can be obtained from a number of sources, including blood and bone marrow fluid. In certain embodiments, any number of monocyte cell lines available in the art, may be used. In certain embodiments, monocyte cells can be obtained from a unit of blood collected from a subject using any number of techniques known to the skilled artisan. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

The monocytes for use in the present invention may be from a specimen containing monocytes. The specimen containing monocytes may be composed of monocytes only. Alternatively, the specimen containing monocytes may be a mixture containing monocytes and a leukocyte component (e.g., lymphocytes, NK cells, or NKT cells) other than monocytes. This mixture may further contain plasma and erythrocytes. The mixture may be a mononuclear cell fraction mainly containing monocytes and lymphocytes prepared from a body fluid sample such as blood by, for example, density gradient centrifugation.

In another embodiment, monocyte cells are isolated from peripheral blood. Alternatively, monocyte cells can be isolated from umbilical cord. In any event, a specific subpopulation of monocyte cells can be further isolated by positive or negative selection techniques.

The cord blood mononuclear cells so isolated can be enriched or depleted of cells expressing certain antigens, including, but not limited to, CD34, CD8, CD14, CD19 and CD56. Enrichment or depletion of these cells can be accomplished using an isolated antibody, a biological sample comprising an antibody, such as ascites, an antibody bound to a physical support, and a cell bound antibody. For example, enrichment of a monocyte cell population by positive CD14$^+$ selection can be accomplished using an antibody directed to CD14 or CD14-microbeads.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

Monocyte cells can also be frozen. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of monocyte cells is comprised within cells such as peripheral blood mononuclear cells, cord blood cells, a purified population of monocyte cells, and a monocyte cell line. In one embodiment, a monocyte cell line is a MonoMac-1 cell line. In another embodiment, peripheral blood mononuclear cells comprise the population of monocyte cells. In yet another embodiment, purified monocyte cells comprise the population of monocyte cells.

Expansion of Monocyte Cells

In one embodiment, expanding the monocyte cells further includes culturing or proliferating the monocyte cells. In another embodiment, the source of the monocyte cells to be expanded is peripheral blood mononuclear cells.

The monocyte proliferating culture medium of the present invention contains at least one of PMA, DEX, MCSF, LPS, TNF-α and IFN-γ. In one embodiment, the monocyte proliferating culture medium of the present invention contains at least 2, at least 3, at least 4, at least 5 or all of PMA, DEX, MCSF, LPS, TNF-α and IFN-γ. In one embodiment, the monocyte proliferating culture medium contains PMA and DEX. In one embodiment, the monocyte proliferating culture medium contains MCSF and LPS. In one embodiment, the monocyte proliferating culture medium contains TNF-α and IFN-γ. In one embodiment, a monocyte cell is expanded in the presence of monocyte proliferating culture medium comprising at least one of PMA and DEX followed by monocyte proliferating culture medium comprising at least one of MCSF and LPS. In one embodiment, a monocyte cell is expanded in the presence of monocyte proliferating culture medium comprising PMA and DEX followed by monocyte proliferating culture medium comprising MCSF and LPS. In one embodiment, the monocyte cell is further expanded in the presence of monocyte proliferating culture medium comprising at least one of TNF-α and IFN-γ.

In one embodiment, the monocyte proliferating culture medium may further contain a nutritional component, a pH adjuster, and other components for enabling culture of monocytes. The culture medium containing such components is not particularly limited, and examples thereof include serum-free synthetic culture media for lymphocytes, AIM-V, and RPMI-1640. The term "culture medium" throughout the specification encompasses media in liquefied prepared forms and also component mixtures (usually powder) before preparation.

Method of Producing Monocytes

The method of producing monocytes of the present invention includes a proliferation step of culturing a monocyte cell in the monocyte proliferating culture medium of the present invention to allow the monocytes to proliferate.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

The monocyte proliferating culture medium may include an agent that can increase the expression of at least one of CD16, CD163 and CD4 in a monocyte cell. For example, monocyte proliferating culture medium may include at least one of PMA, LPS, MCSF, DEX, TNFα and IFNγ in any amount effective to increase the expression of at least one of CD16, CD163 and CD4 in a monocyte cell.

The monocyte proliferating culture medium of the present invention may contain a reagent that is usually used in cell culture. Examples of the reagent include antibiotics (e.g., gentamycin and kanamycin), albumin, and serum (e.g., fetal bovine serum). The monocyte proliferating culture medium of the present invention may contain autologous plasma (i.e., the monocytes to be proliferated and the autologous plasma are collected from the same body) derived from a living body (mammals such as human, porcine, bovine, horse, goat, sheep, rabbit, or monkey). Furthermore, the monocyte proliferating culture medium of the present invention may contain a material for promoting differentiation of the monocytes of the invention.

Proliferation Step

The proliferation step according to the present invention may be performed under any condition without particular limitation, and from the viewpoint of allowing monocytes to proliferate before the start of differentiation of a lot of monocytes, the culture is preferably performed under conditions of 30° C. to 40° C. and 2% to 8% $CO_2$. The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days. During the culture, replacement of the culture medium may be appropriately carried out by a known method.

The monocyte cells may be proliferated by the methods disclosed herein such that the original number of monocytes can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween.

In one embodiment, according to the method of producing monocytes of the present invention, the monocytes can proliferate to an amount allowing clinical use (e.g., $10^6$ to $10^7$ cells/mL or more). In one embodiment, the amount allowing clinical use refers to an amount of monocytes proliferated such that dendritic cells differentiated from the proliferated monocytes can be used as a dendritic cell vaccine.

In the method of producing monocytes of the present invention, monocytes are cultured in the monocyte proliferating culture medium of the present invention, that is, monocytes are proliferated under conditions that increase the expression level of at least one of CD16, CD163 and CD4. Therefore, in one embodiment the method of producing monocytes of the present invention can provide a population of monocytes with an increased percentage of monocytes expressing at least one of CD16, CD163 and CD4. In one embodiment, at least 10%, 15%, 20%, 25%, 30%, 35%, 40%, 45%, 50%, 55%, 60%, 65%, 70%, 75%, 80%, 85%, 90%, 95%, or greater than 95% of the monocytes proliferated in the monocyte proliferating culture medium of the present invention expressing at least one of CD16, CD163 and CD4.

In one embodiment, the method provides a monocyte cell having an increased level of expression of at least one of CD16, CD163 and CD4. In one embodiment, the expression of at least one of CD16, CD163 and CD4 is increased by at least 1.1 fold, 1.2 fold, 1.3 fold, 1.4 fold, 1.5 fold, 1.6 fold, 1.7 fold, 1.8 fold, 1.9 fold, 2.0 fold, 2.5 fold, 3.0 fold, 3.5 fold, 4.0 fold, 5.0 fold, 6.0 fold, 7.0 fold, 8.0 fold, 9.0 fold, 10 fold, 15 fold, 20 fold, 25 fold, 30 fold, 35 fold, 40 fold, 45 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween, in a monocyte cell cultured in the monocyte proliferating culture medium of the present invention over the expression level of a monocyte cell that is not proliferated in the monocyte proliferating culture medium of the present invention.

Following culturing, the monocyte cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. A period of time can be any time suitable for the culture of cells in vitro. The monocyte cell medium may be replaced during the culture of the monocyte cells at any time. Preferably, the monocyte cell medium is replaced about every 2 to 3 days. The monocyte cells are then harvested from the culture apparatus whereupon the monocyte cells can be used immediately or cryopreserved to be stored for use at a later time. In one embodiment, the invention includes cryopreserving the expanded monocyte cells. The cryopreserved, expanded monocyte cells are then thawed prior to further use (e.g., culturing for further use in any appropriate assay or differentiation).

Differentiation of Monocyte Cells

In various embodiments, the invention relates to cells that result from the differentiation of a monocyte cell of the invention. In one embodiment, the monocytes of the invention may differentiate into monocytes or dendritic cells. Therefore, in one embodiment, the invention provides a population of dendritic cells derived from a monocyte cell of the invention. In one embodiment, the invention provides a population of monocyte cells derived from a monocyte cell of the invention.

The method of differentiating monocytes into dendritic cells is a conventionally known step. That is, monocytes are differentiated into immature dendritic cells by culture in a culture medium for differentiation containing, for example, IL-4. The resultant immature dendritic cells are differentiated into mature dendritic cells by culture in a culture medium containing, for example, TNF-α. The term "dendritic cell" in the present invention encompasses both an immature dendritic cell and a mature dendritic cell.

A monocyte tends to differentiate into a macrophage in the presence of granulocyte macrophage colony-stimulating factor (GMCSF) and tends to differentiate into a dendritic cell in the presence of GMCSF and IL-4. The investigation by the present inventors, however, revealed a fact that the monocyte proliferating culture medium of the present invention containing GMCSF can considerably accelerate proliferation of monocytes. It has been conventionally known that GMCSF itself also has an effect of allowing proliferation of monocytes, however, the monocyte proliferating culture medium of the present invention containing GMCSF can considerably accelerate proliferation of monocytes without differentiating the monocytes. In addition, the monocyte proliferating culture medium of the present invention may further contain IL-4 in an amount less than the amount allowing differentiation of monocytes into dendritic cells (e.g., 500 to 2000 IU/mL), in addition to GMCSF. The amount of GMCSF contained in the monocyte proliferating culture medium of the present invention is, for example, within a range of 500 to 2000 IU/mL.

In one embodiment, the monocyte proliferating culture medium of the present invention may further contain a cytokine involved in differentiation of monocytes, including but not limited to GMCSF, IL-4 or a combination thereof Modified Monocytes In one embodiment, the invention relates to monocytes that have been modified to have increased level or activity of at least one of CD16, CD163 and CD4.

It will be understood by one skilled in the art, based upon the disclosure provided herein, that an increase increased level or activity of at least one of CD16, CD163 and CD4 encompasses the increase in expression, including transcription, translation, or both of at least one of CD16, CD163 and CD4. The skilled artisan will also appreciate, once armed with the teachings of the present invention, that an increase in the level of at least one of CD16, CD163 and CD4 includes an increase in activity at least one of CD16, CD163 and CD4. Thus, increasing the level or activity of at least one of CD16, CD163 and CD4 includes, but is not limited to, increasing the amount of at least one of CD16, CD163 and CD4 polypeptide, increasing transcription, translation, or both, of a nucleic acid encoding at least one of CD16, CD163 and CD4 and it also includes increasing any activity of at least one of CD16, CD163 and CD4 polypeptide as well.

Therefore, in one embodiment, the invention relates to modified monocyte cells having been modified with at least one isolated nucleic acid comprising a nucleotide sequence encoding CD16, CD163 or CD4.

In another aspect, the invention relates to a construct, comprising a nucleotide sequence encoding a CD16, CD163 or CD4. In a particular embodiment, the construct is operatively bound to transcription, and optionally translation, control elements. The construct can incorporate an operatively bound regulatory sequence of the expression of the nucleotide sequence of the invention, thus forming an expression cassette.

A nucleotide sequence encoding a CD16, CD163 or CD4 may be prepared using recombinant DNA methods. Accordingly, nucleic acid molecules which encode CD16, CD163 or CD4 may be incorporated in a known manner into an appropriate expression vector which ensures good expression of the protein.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6N5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., "Molecular cloning, a Laboratory Manual", 2nd ed., Cold Spring Harbor Laboratory Press, N.Y., 1989 Vol 1-3]. In a particular embodiment, the vector is a vector useful for transforming animal cells.

Recombinant expression vectors may be introduced into host cells to produce a recombinant cell. The vector of the invention can be used to transform a monocyte cell of the invention. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

Methods of Identifying a Modulator of CD16, CD163 or CD4

In one embodiment, the current invention relates to methods of identifying a compound that modulates the level or activity of at least one of CD16, CD163 or CD4. In some embodiments, the method of identifying of the invention identifies an inhibitor compound that decreases the level or activity of at least one of CD16, CD163 or CD4. In other embodiments, the method of identifying of the invention identifies an activator compound that increases the activity of at least one of CD16, CD163 or CD4.

In one embodiment, the method comprises contacting a monocyte, or a cell derived therefrom, of the invention with a test compound and evaluating the effect of the test compound on the level or activity of at least one of CD16, CD163 or CD4.

Other methods, as well as variation of the methods disclosed herein will be apparent from the description of this invention. In various embodiments, the test compound concentration in the screening assay can be fixed or varied. A single test compound, or a plurality of test compounds, can be tested at one time. In some embodiments, the method of identifying is a high-throughput screen. Suitable test compounds that may be used include, but are not limited to, proteins, nucleic acids, antisense nucleic acids, shRNA, small molecules, antibodies and peptides.

The invention relates to a method for screening test compounds to identify a modulator compound by its ability to modulate (i.e., increase or decrease) the level of activity of at least one of CD16, CD163 or CD4, in the presence and absence of the test compound. The activity of at least one of CD16, CD163 or CD4 that is assessed can be any measurable activity of the protein.

Test compounds that can be assessed in the methods of the invention include a chemical compound, a protein, a peptide, a peptidomemetic, an antibody, a nucleic acid, an antisense nucleic acid, an siRNA, a miRNA, a shRNA, a ribozyme, an allosteric modulator, and a small molecule chemical compound.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223, 409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical to that new chemical entities with useful properties are generated by identifying a chemical compound (called a "lead compound") with some desirable property or activity, creating variants of the lead compound, and evaluating the property and activity of those variant compounds.

In one embodiment, high throughput screening methods involve providing a library containing a large number of test compounds potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

In one embodiment, a compound identified as a potential therapeutic using a screen of the invention is a compound that inhibits CD16. In one embodiment, the compound that inhibits CD16 is one of a chemical compound, a protein, a peptide, a peptidomemetic, an antibody, a nucleic acid, an antisense nucleic acid, an siRNA, a miRNA, a shRNA, a ribozyme, an allosteric modulator, and a small molecule chemical compound.

In one embodiment, a compound identified as a potential therapeutic using a screen of the invention is a compound that inhibits CD163. In one embodiment, the compound that inhibits CD163 is one of a chemical compound, a protein, a peptide, a peptidomemetic, an antibody, a nucleic acid, an antisense nucleic acid, an siRNA, a miRNA, a shRNA, a ribozyme, an allosteric modulator, and a small molecule chemical compound.

Therapy

In one embodiment, the monocyte cells, or cells derived therefrom, as described herein may be included in a composition for therapy.

In one embodiment, a compound identified in a screen using the monocyte cells, or cells derived therefrom, as described herein may be included in a composition for therapy. In one embodiment, the compound for use in a composition for therapy comprises an inhibitor of CD16. In one embodiment, the compound for use in a composition for therapy comprises an inhibitor of CD163.

In one embodiment, the composition may include a pharmaceutical composition and further include a pharmaceutically acceptable carrier. A therapeutically effective amount of the pharmaceutical composition comprising a monocyte cell, cells derived therefrom, or a compound identified from a screen of the invention may be administered to a subject in need thereof.

In one embodiment, a monocyte cell, cells derived therefrom, or a compound identified from a screen of the invention may be used for the manufacture of a medicament for the treatment of a disease or disorder in a subject in need thereof. In one embodiment, a disease or disorder is associated with inflammation and immune activation.

The therapeutic composition of the invention can be administered to an animal, preferably a mammal, even more preferably a human, to treat a disease or disorder. For example, the cells of the present invention, cells derived therefrom, or a compound identified from a screen of the invention, can be used for the treatment of any condition related to inflammation and an activated immune response.

In one embodiment, a disease or disorder that can be treated using the compositions of the invention is a cancer. Examples of cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like.

In one embodiment, a disease or disorder that can be treated using the compositions of the invention is a disease associated with inflammation. Examples of diseases associated with inflammation include, but are not limited to, allergy, arthritis, rheumatoid arthritis, asthma, autoimmune diseases, celiac disease, chronic kidney disease (CKD), IgA nephropathy, Crohn's disease (CD), diabetes, glomerulonephritis, chronic hepatitis C and other liver diseases, inflammatory bowel diseases (IBD), reperfusion injury, ulcerative colitis (UC), transplant rejection, amyotrophic lateral sclerosis, lupus, multiple sclerosis, tuberculosis, sarcoidosis, common variable immune deficiency, atherosclerosis, cardiovascular disease, heart failure, aging, and other diseases associated with an expansion of proinflammatory $CD14^+$ $CD16^+$ monocytes.

Cells of the invention, or cells derived therefrom, can be administered in dosages and routes and at times to be determined in appropriate pre-clinical and clinical experimentation and trials. Cell compositions may be administered multiple times at dosages within these ranges. Administration of the cells of the invention may be combined with other methods useful to treat the desired disease or condition as determined by those of skill in the art.

The cells to be administered may be autologous, allogeniec or xenogenic with respect to the subject undergoing therapy.

The administration of the therapeutic composition of the invention may be carried out in any convenient manner known to those of skill in the art. The therapeutic composition of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the therapeutic compositions of the invention are injected directly into a site of inflammation in the subject, a local disease site in the subject, a lymph node, an organ, a tumor, and the like.

The therapeutic compositions described herein can also be administered using any number of matrices. Such matrices may act, for example, as an artificial lymphoid organ to support, maintain, or modulate the immune system. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

Pharmaceutical Compositions

Pharmaceutical compositions of the present invention may comprise a monocyte cell population as described herein, or a population of cells derived from a monocyte cell of the invention, or a compound identified in a screen of the invention, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

It can generally be stated that a pharmaceutical composition comprising the monocyte cells, cells derived therefrom, or a compound identified in a screen of the invention, described herein may be administered at a dosage of $10^4$ to $10^9$ cells/kg body weight, preferably $10^5$ to $10^6$ cells/kg body weight, including all integer values within those ranges. The cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments of the present invention, cells expanded using the methods described herein or a compound identified in a screen of the invention, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the monocyte cells, or cells derived therefrom, of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Culture of Animal Cells" (Freshney, 2010); "Methods in Enzymology" "Handbook of Experimental Immunology" (Weir, 1997); "Short Protocols in Molecular Biology" (Ausubel, 2002); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Kits

The present invention also pertains to kits useful in the methods of the invention. Such kits comprise various combinations of components useful in any of the methods described elsewhere herein, including for example, a monocyte proliferating culture medium of the invention, or a monocyte or cell derived therefrom of the invention, and instructional material. For example, in one embodiment, the kit comprises components useful for the quantification of at least one of CD16, CD163 and CD4 in a biological sample. In a further embodiment, the kit comprises components useful for the assessment of the activity (e.g., enzymatic activity, substrate binding activity, etc.) of at least one of CD16, CD163 and CD4 in a biological sample.

In various embodiments, to determine whether the level of at least one of CD16, CD163 and CD4 is modulated in a sample, the level of at least one of CD16, CD163 and CD4 is compared with the level of at least one comparator control contained in the kit, such as a positive control, a negative control, a historical control, a historical norm, or the level of another reference molecule in the biological sample.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Differentiation of MonoMac-1 Cell Line Induced by MCSF and Glucocorticoid Pathways In the work described here, a cell line derived from an Acute Myelogenous Leukemia (AML) cell line, MONO-MAC-1, was grown under conditions to promote the expression of CD16 and CD163. These conditions appear to involve the glucocorticoid pathway as well as cFMS signaling based on the action of dexamethasone and macrophage colony stimulating factor-1 in promoting $CD16^+$ expression, in addition to PMA and LPS treatment. The ability of glucocorticoid and cFMS receptor antagonists to inhibit $CD16^+$ cell formation further establishes the role of these pathways in CD16 expression in this cell line. The process used to induce CD16 expression in this cell type will be useful for screening and identification of drug candidates potentially useful for treatment of diseases where the etiology involves the expansion of the $CD16^+$ monocytes subset or the accumulation of $CD163^+/CD16^+$ tissue macrophages. In addition, the invention provides an experimental system for drug screening or evaluating drug candidates where the modulation of CD16 and CD163 is desired.

The materials and methods employed in these experiments are now described.

Materials and Methods

MONO-MAC-1 cells were cultured at 37° C. in a humidified atmosphere containing 5% $CO_2$ using RPM1 1640 medium supplemented with 10% heat-inactivated fetal bovine serum (FBS, Sigma) and 1% of stable glutamine, 1 mM sodium pyruvic acid and 1×MEM non-essential amino acids were added. Cells were seeded at a density of 0.5×106 cells/ml and were sub cultured upon reaching $1 \times 10^6$ cells/ ml. Medium was changed every 2 to 3 days. For differentiation of MONOMAC-1 into a monocyte/macrophage-like phenotype, the cells were treated with 20 ng/ml phorbol-12-myristate-13-acetate (PMA) alone and combine with 10 ng/ml lipopolysaccharide (LPS) for 72 h at a density of $0.5 \times 10^6$ cells/ml. after 72 hours they wash and incubated in MCSF and Dexamethasone (DEX) with 5 ng/ml and 200 ng/ml respectively for 4 days. In some experiments, following 4 days of incubation with MCSF and DEX, RU486 and PLX3397, a glucocorticoid (GR) and c-fms antagonist respectively, were added to the culture medium at a final concentration of 500 nM to block glucocorticoid signaling and c-fms receptor. Data were analyzed with GraphPad Prism (version 6) soft-ware. Flow cytometric measurements were performed using four colors FACSCalibur (Becton Dickinson).

The results of the experiments are now described.

Figure 1C:
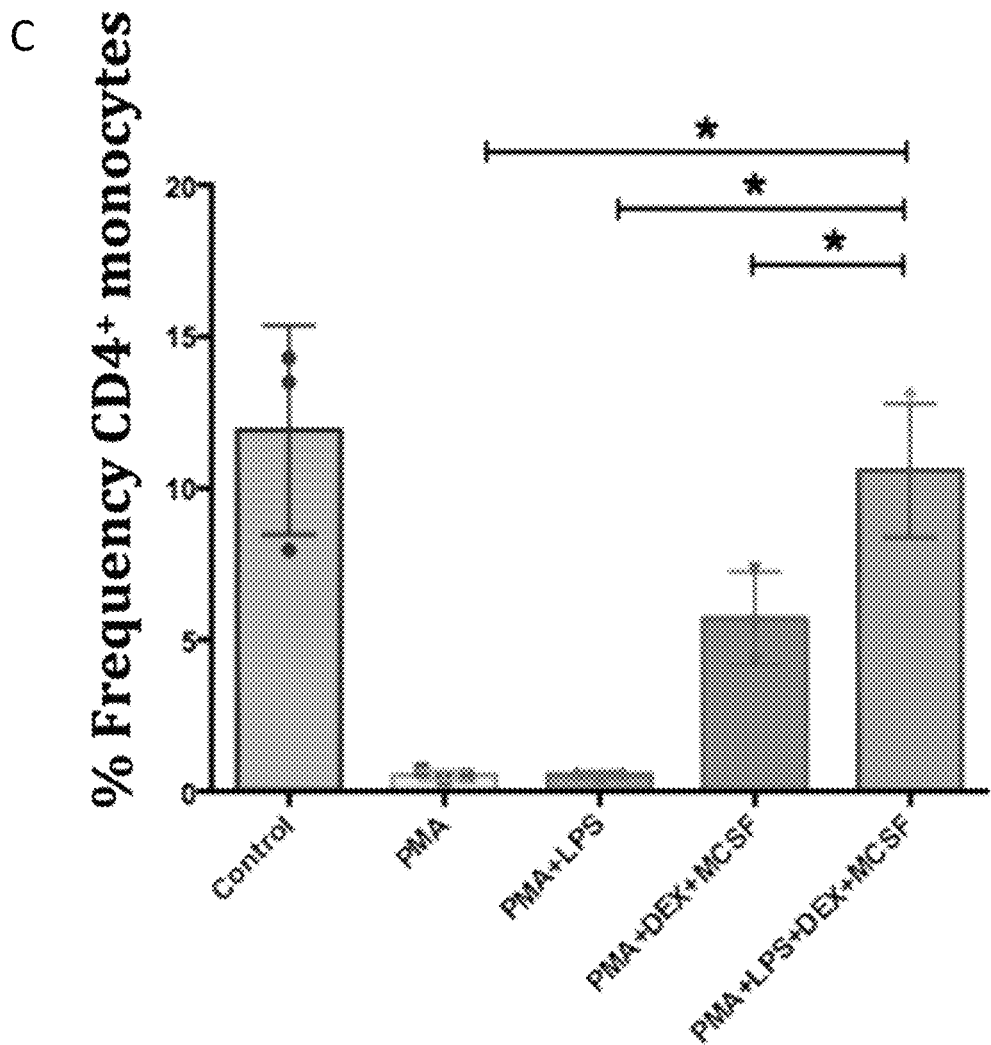

The combination of MCSF, DEX, PMA and LPS increase the frequency of expression of CD16+CD163+CD4+ human monocytes in vitro (FIG. 1). Although, combination of DEX, MSCF and PMA increases expression of $CD163^+$ significantly, addition of LPS has the most effect on expression $CD163^+$ (FIG. 1A). Expression of $CD16^+$ and $CD4^+$ was increased with combination of PMA+LPS+DEX+MCSF as compared to other treatment conditions. (*p=<0.05 and ** p=<0.01) (FIG. 1B and FIG. 1C).

Figure 2A:
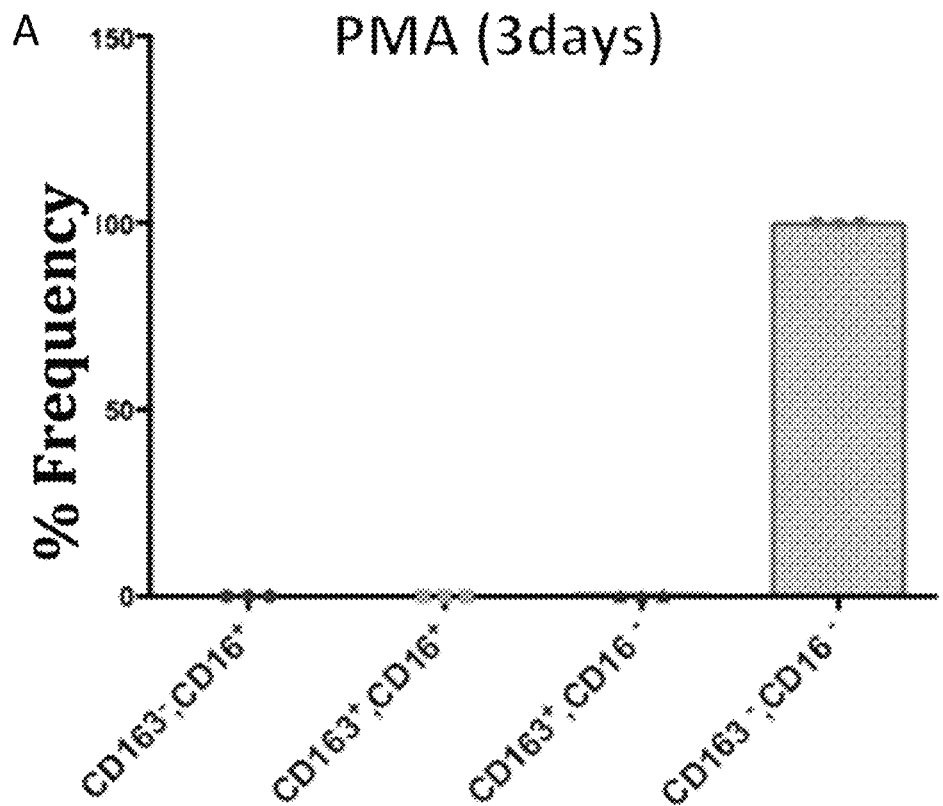
FIG. 2A through FIG. 2D, depicts experimental results demonstrating that the combination of MCSF, DEX, PMA and LPS increase the frequency of expression area of $CD16^+$ $CD163^+$ human monocytes in vitro. For FIG. 2A through FIG. 2D, CD163 and CD16 monocytes in different treatment conditions were analyzed by flow cytometry.
Figure 2B:
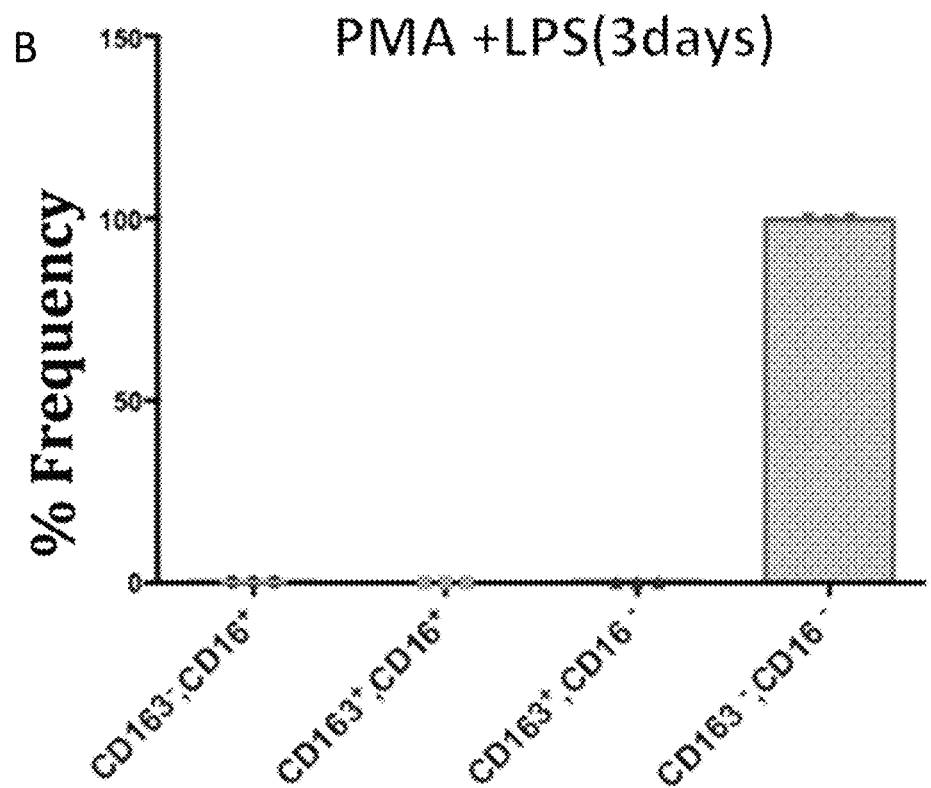
Figures 2C, 2D:
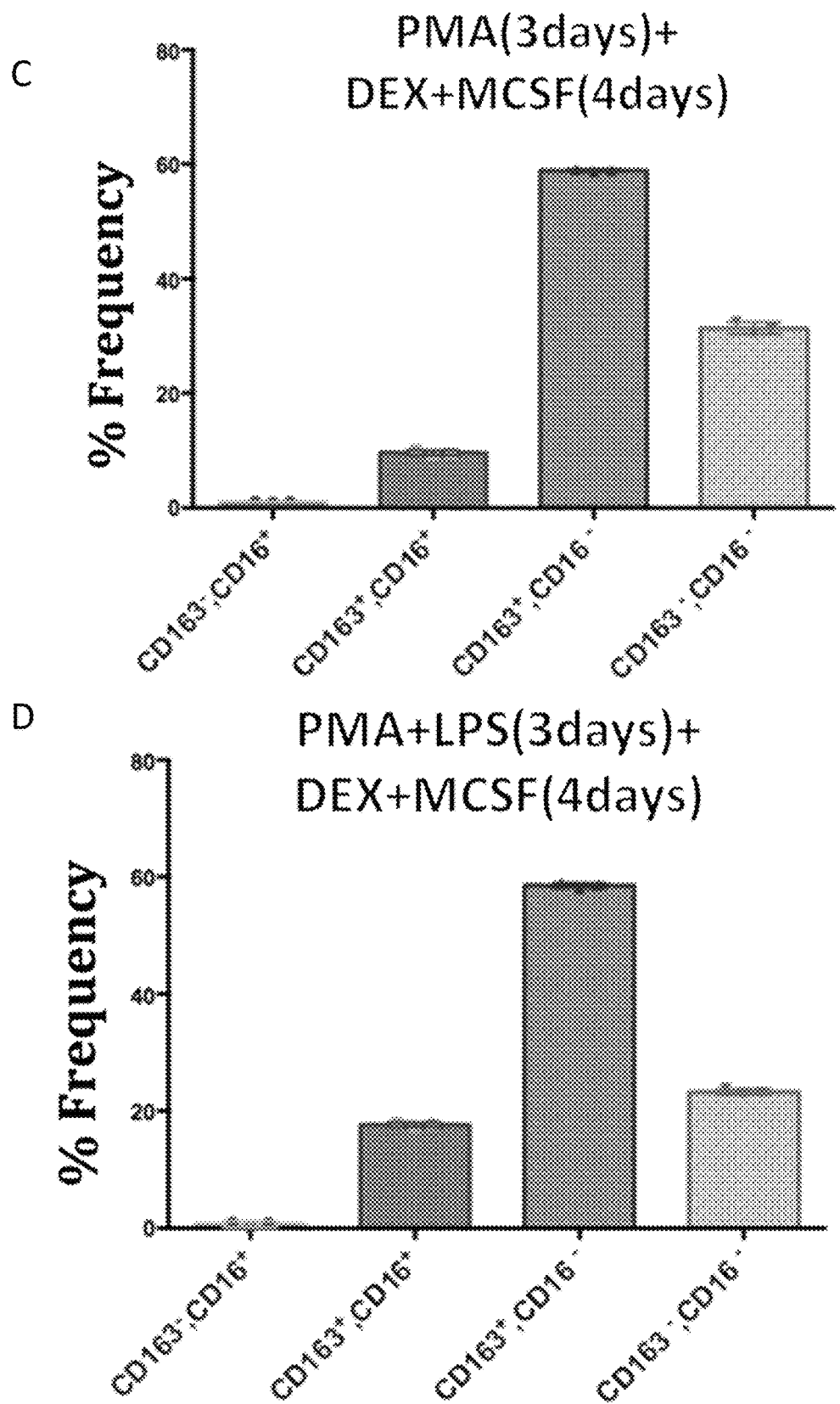
Figures 3A, 3B, 3C, 3D:
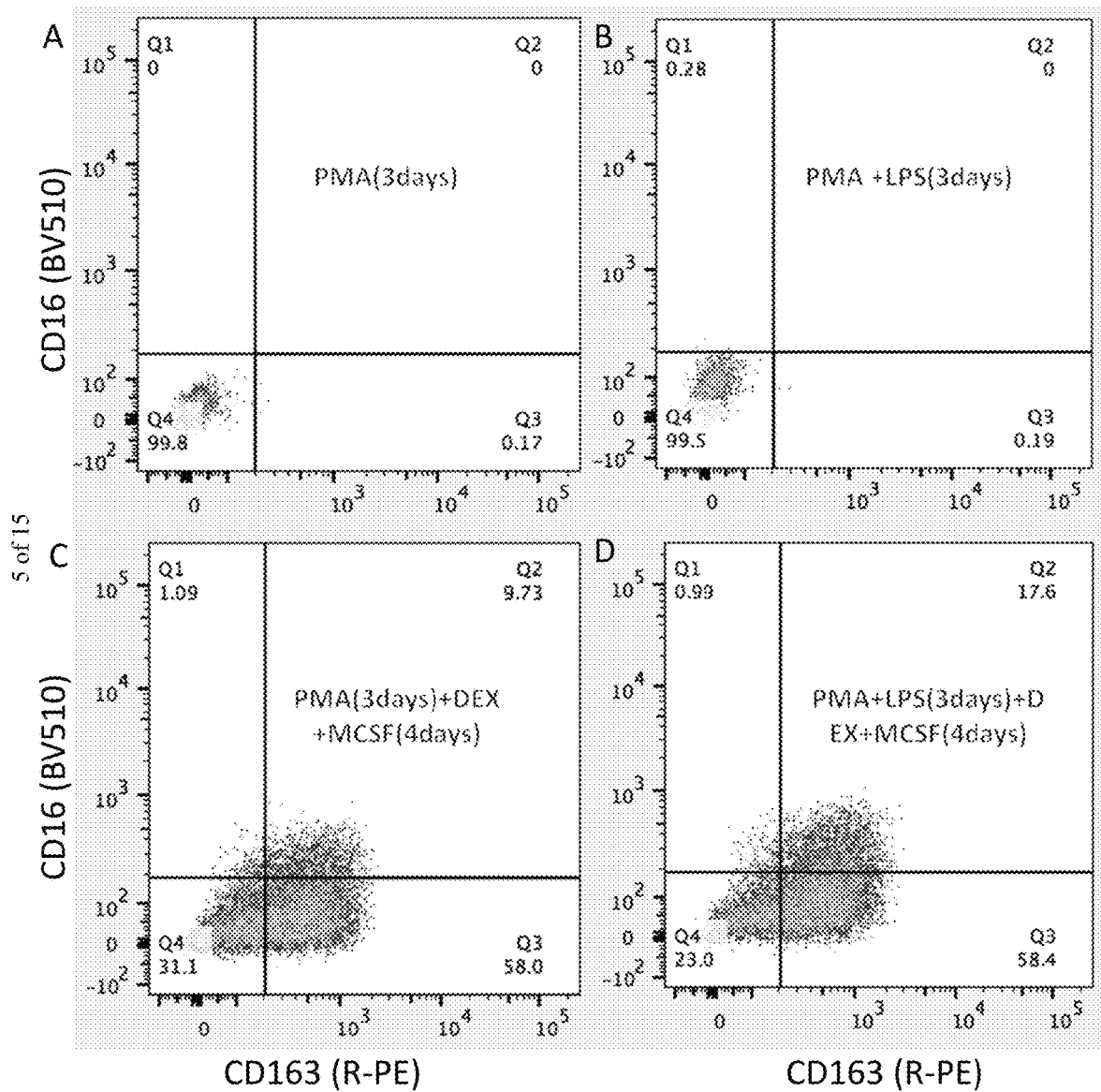
FIG. 3A through FIG. 3D, depicts representative dot plot graphs demonstrating that the combination of MCSF, DEX, PMA and LPS increase the frequency of expression of $CD16^+$ $CD163^+$ human monocytes in vitro. For FIG. 3A through FIG. 3D, CD163 and CD16 monocytes in different treatment conditions were analyzed by flow cytometry.

The combination of MCSF, DEX, PMA and LPS increases the percentage of $CD16^+$ $CD163^+$ human monocytes in vitro (FIG. 2D and FIG. 3D). An increase in the frequency of $CD163^+$, $CD16^+$ and $CD4^+$ monocytes in MONOMAC-1 cells were sequentially treated with PMA, LPS, DEX and MCSF and based on the data this treatment has the most effect on the expression of $CD163^+$ monocytes ($CD14^+$). Although the combination of PMA, DEX and MCSF has the most effect on expression of all CD163 CD16 gates, addition of LPS is required to have maximum effect on expression of $CD163^+$ $CD16^+$ (FIG. 3C vs FIG. 3D).

Figure 4A:
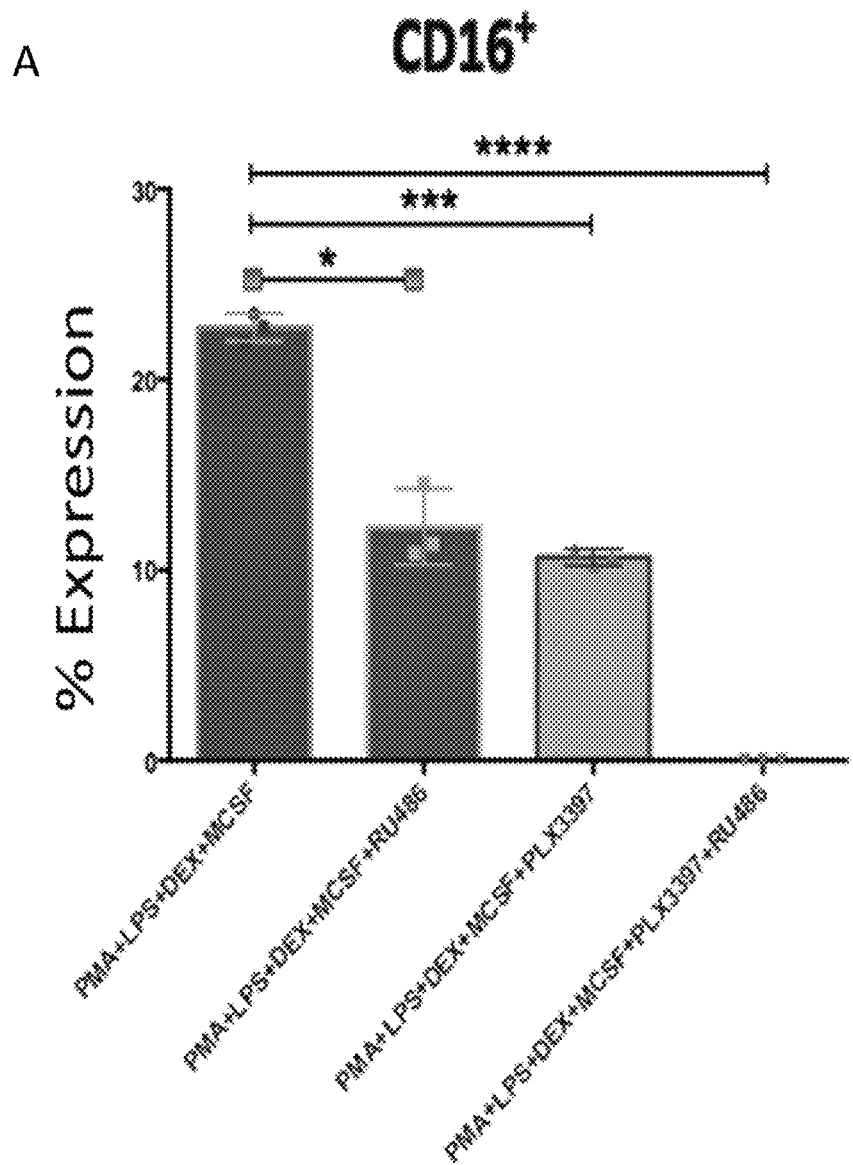
FIG. 4A through FIG. 4C, depicts experimental results demonstrating that blocking the activation of glucocorticoid and c-fms receptors by RU486 and PLX3397 leads to a reduction in expression of $CD16^+$ $CD163^+$ and $CD4^+$.
Figure 4B:
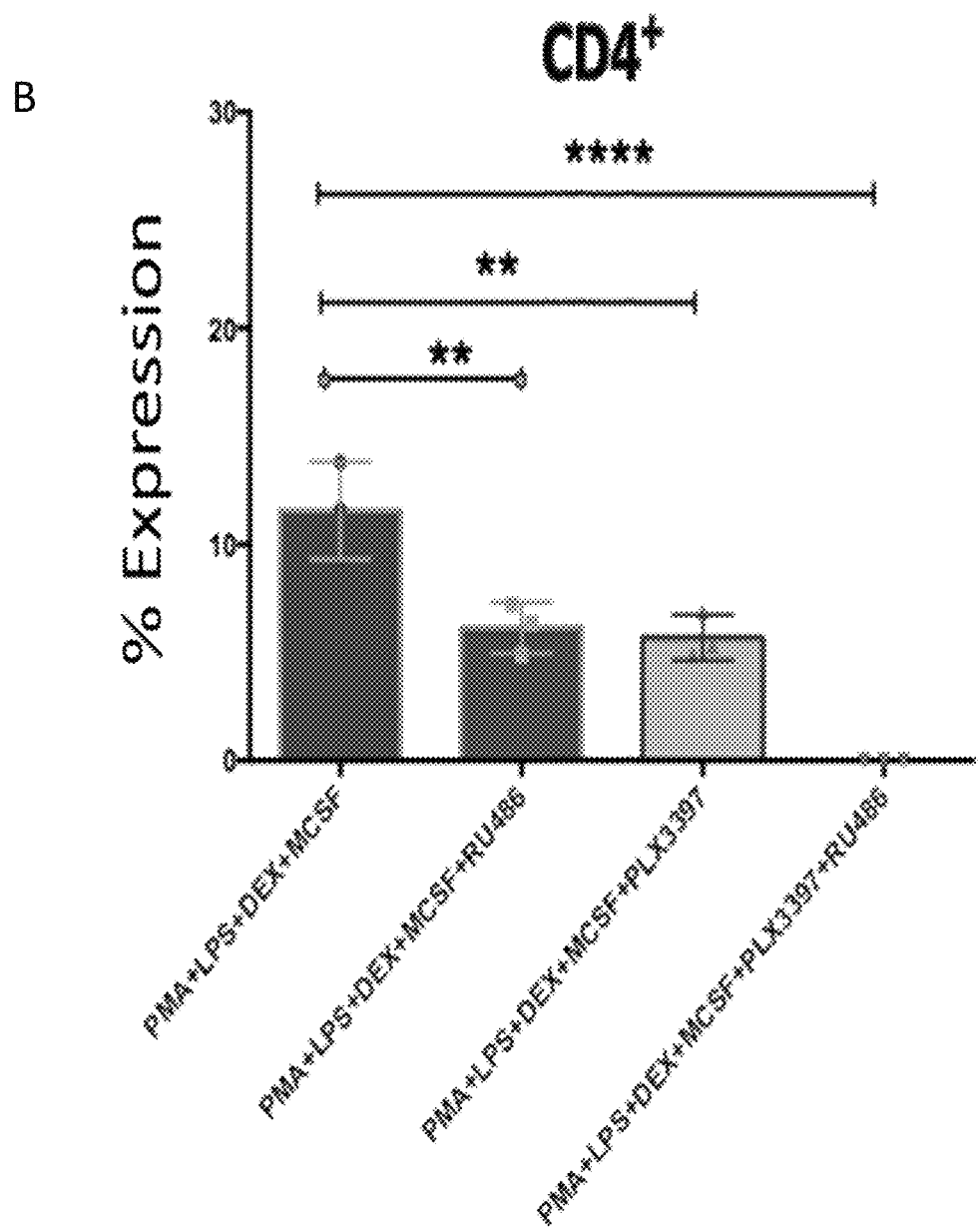
Figure 4C:
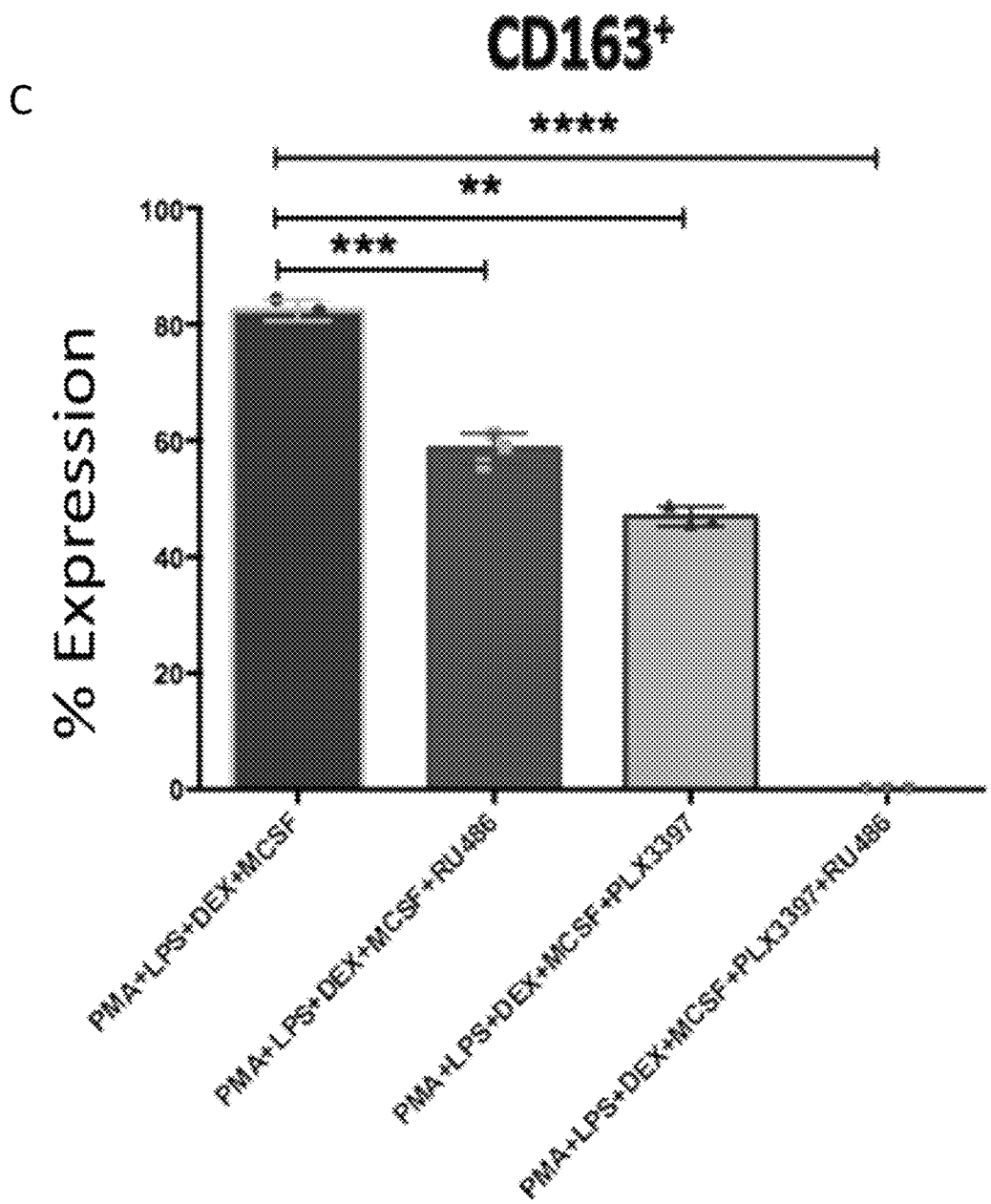

Blocking the activation of glucocorticoid and c-fms receptors by RU486 and PLX3397 respectively led to a reduction in expression of $CD163^+$, $CD16^+$, and $CD4^+$ in monocytes (FIG. 4). The glucocorticoid receptor antagonist RU486 decreases the expression of $CD4^+$, $CD 16^+$ and $CD163^+$. MCSF promotes expression of $CD163^+$ by monocytes, and PLX3397, an inhibitor of c-fms, significantly decreases expression of $CD163^+$.

Figures 5A, 5B, 5C:
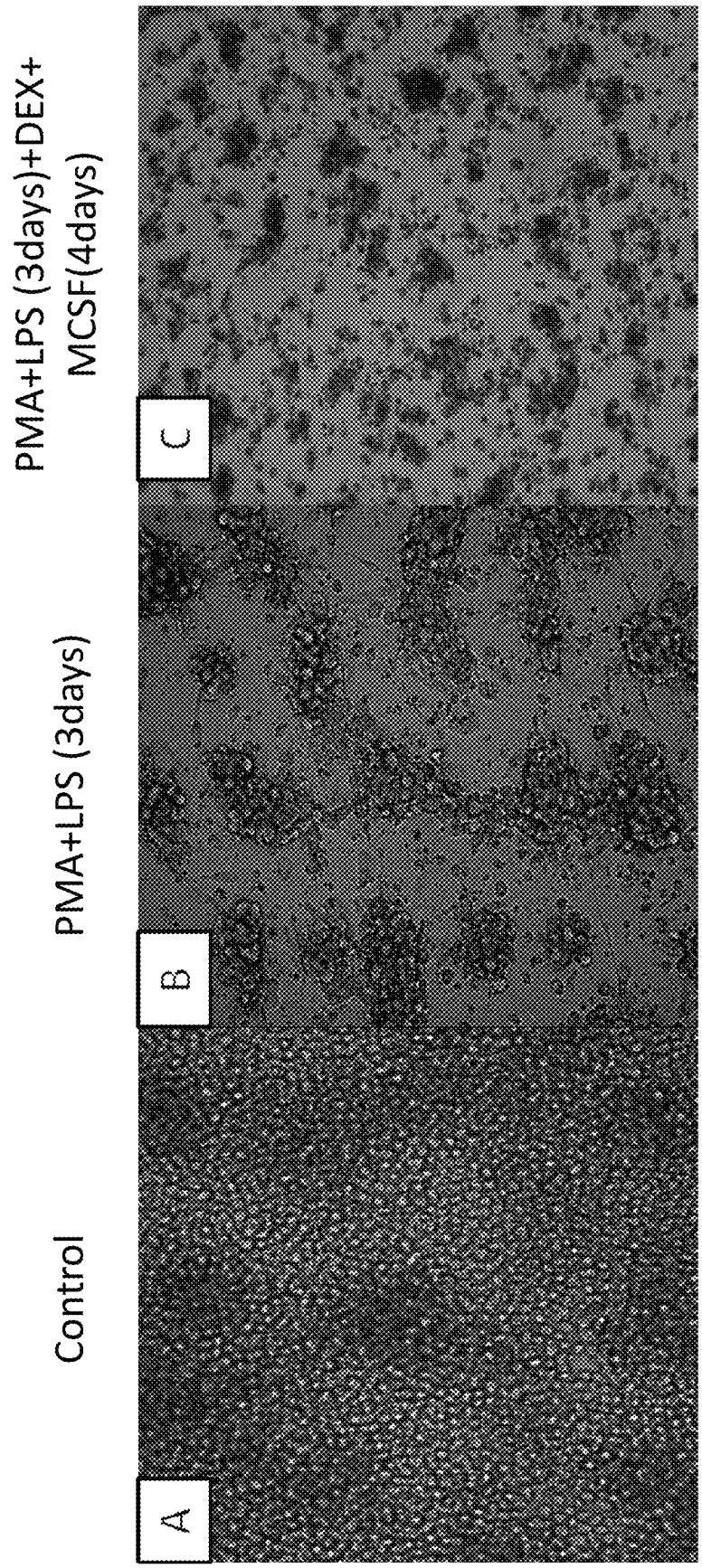
FIG. 5A through FIG. 5C, depicts representative images showing the morphologic changes of MonoMac-1 differentiation under the different treatment conditions.

MonoMac-1 cells show different levels of differentiation under the different treatment conditions (FIG. 5).

An increase in the frequency of $CD163^+$, $CD16^+$ and $CD4^+$ monocytes in MONOMAC-1 cells were sequentially treated with PMA, LPS, DEX and MCSF and based on the data, this treatment regime provides a means for differentiation of these cells with the expression CD163 and CD16 surface markers.

Although the combination of PMA, DEX and MCSF has the most effect on expression of all CD163 CD16 gates, addition of LPS is required to have maximum effect on expression of $CD163^+$ $CD16^+$.

The glucocorticoid receptor antagonist RU486 decreases the expression of $CD4^+$, $CD 16^+$ and $CD163^+$.

MCSF promotes expression of $CD163^+$ by monocytes, and PLX3397 as inhibitor of c-fms significantly decreases expression of $CD163^+$.

CD163+/CD16+ monocytes have been found to be expanded in a variety of disease states and thus this model provides a means for interrogation and drug discovery.

A major mechanism for inflammation and disease pathogenesis involves tryptophan catabolism via the kynurenine pathway. As such we evaluated cytokine inducers of IDO enzyme induction, a limiting step in the kynurenine pathway.

Figure 6A:
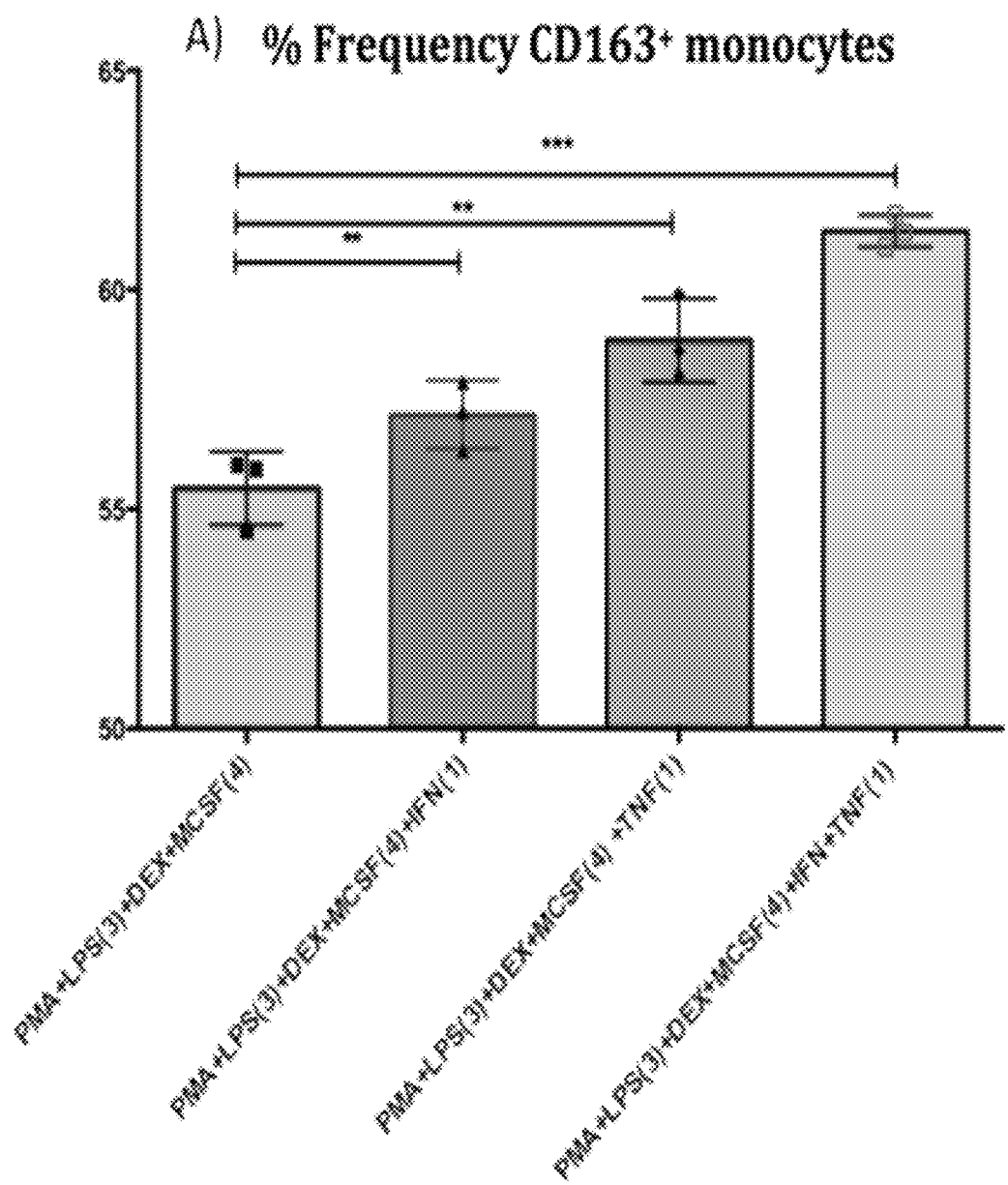
FIG. 6A through FIG. 6B, depicts the results of exemplary experiments demonstrating that TNFα and IFNγ increasing the frequency of $CD163^+$ and $CD16^+$ MonoMac-1 cells. TNFα and IFNγ for 24 hours with and without washing was added to MonoMac-1 was treated with PMA+DEX+MCSF+LPS.
Figure 6B:
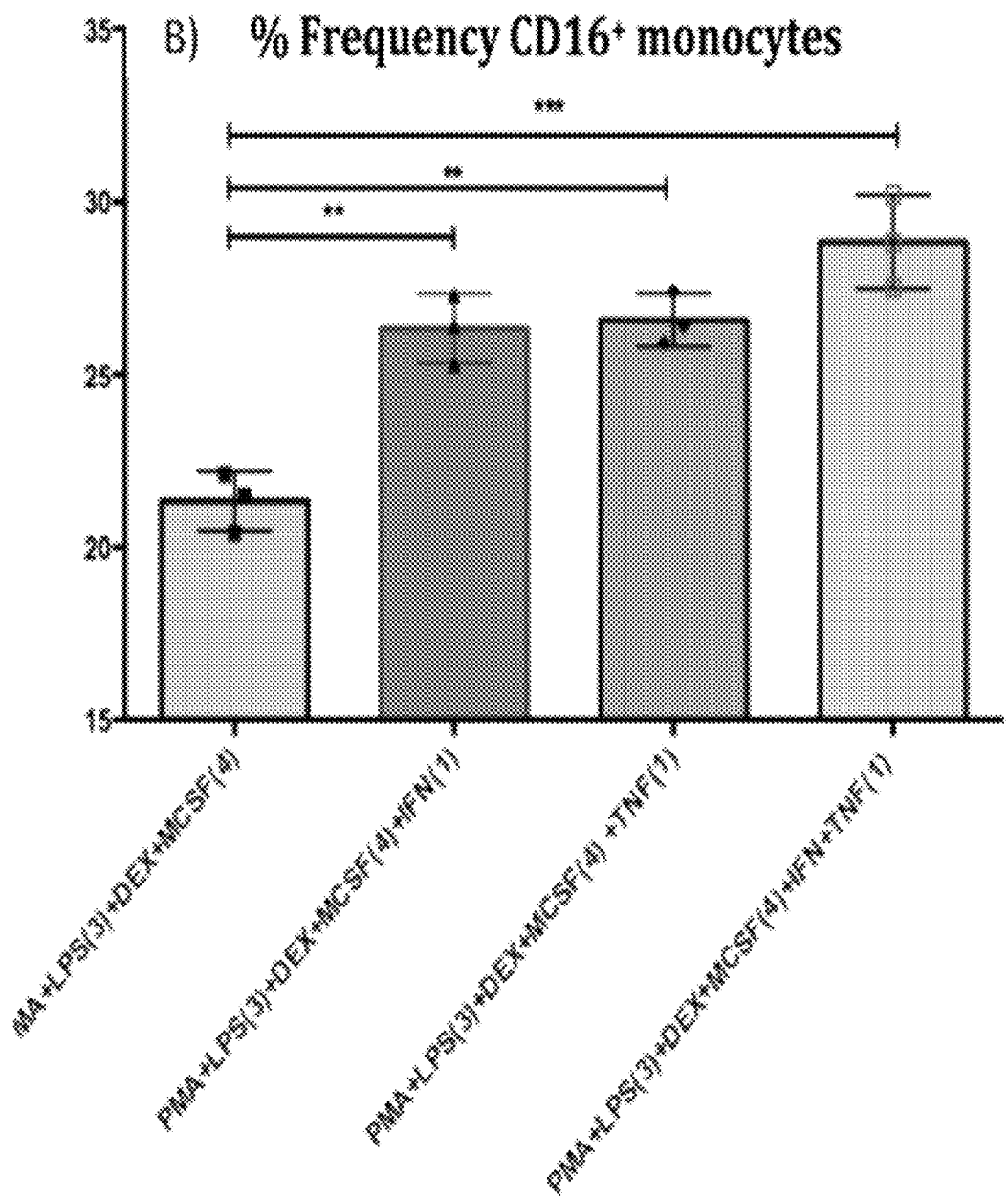

TNF α and IFN γ further increase the expression of $CD16^+$ and $CD163^+$ (FIG. 6).

Figure 7A:
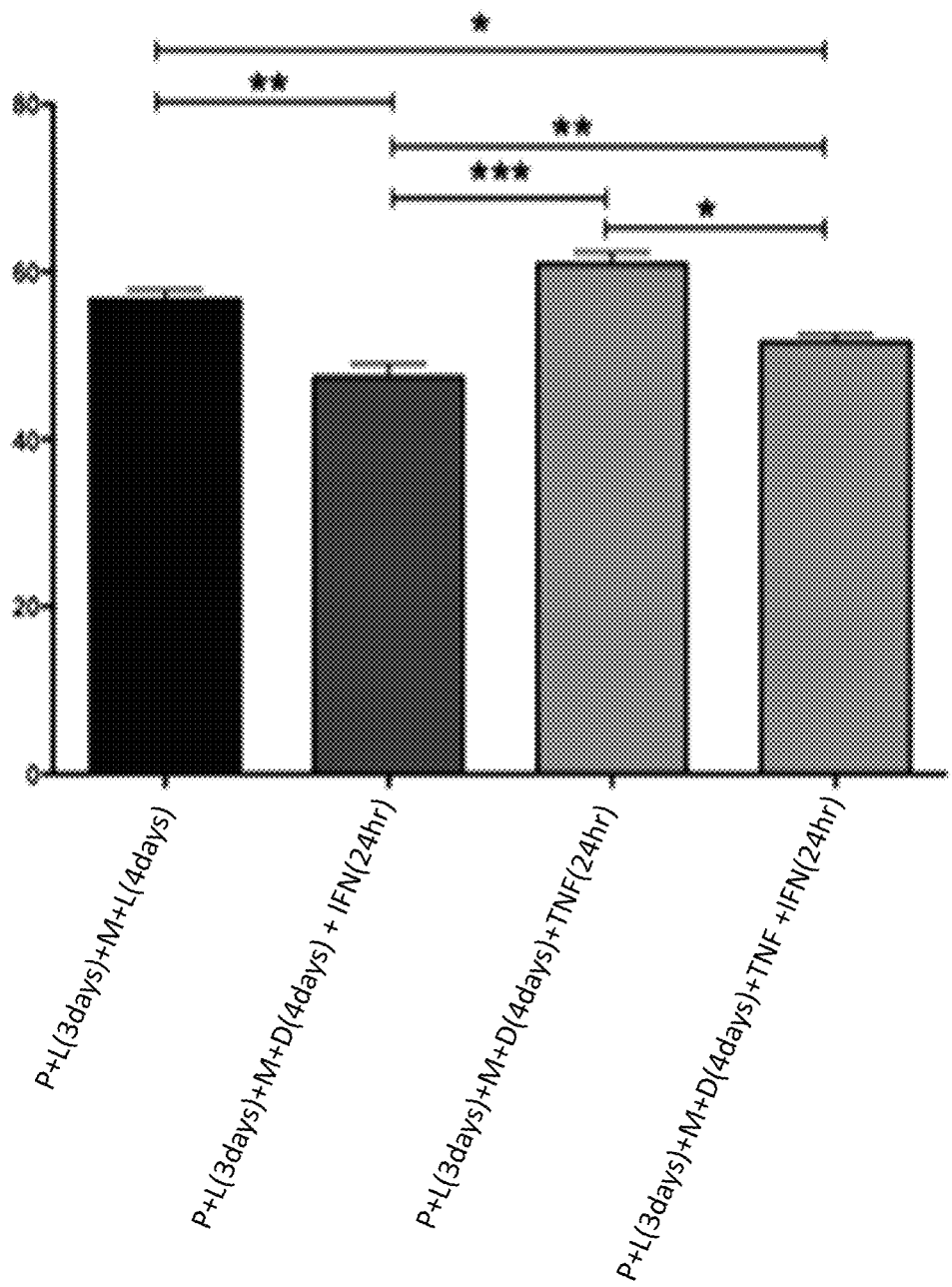
FIG. 7A through FIG. 7C, depicts the results of exemplary experiments demonstrating the effect of TNFα and IFNγ on tryptophan, kynurenine, and the kynurenine to tryptophan (KT) ratio in MonoMac-1.
Figure 7B:
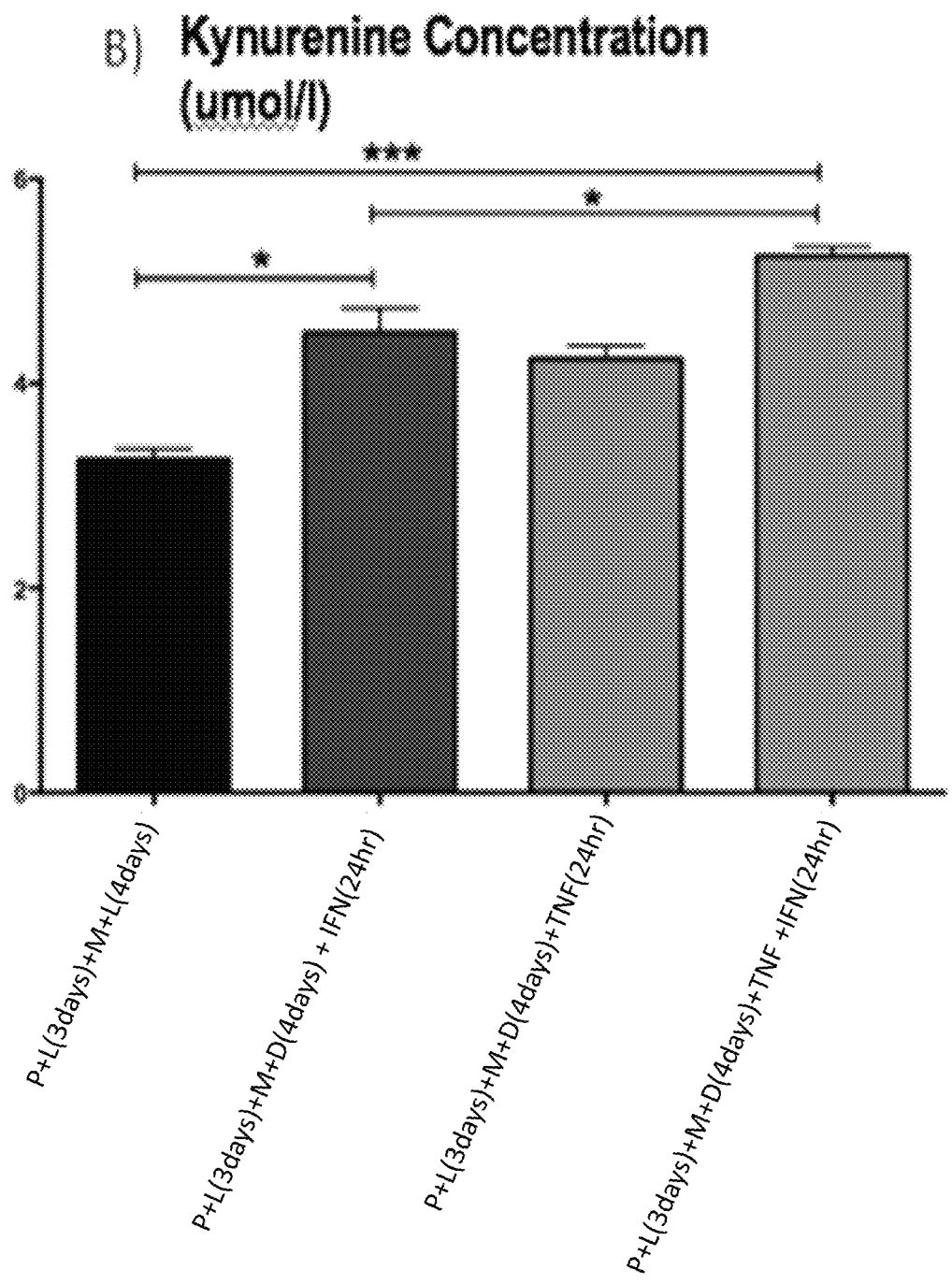
Figure 7C:
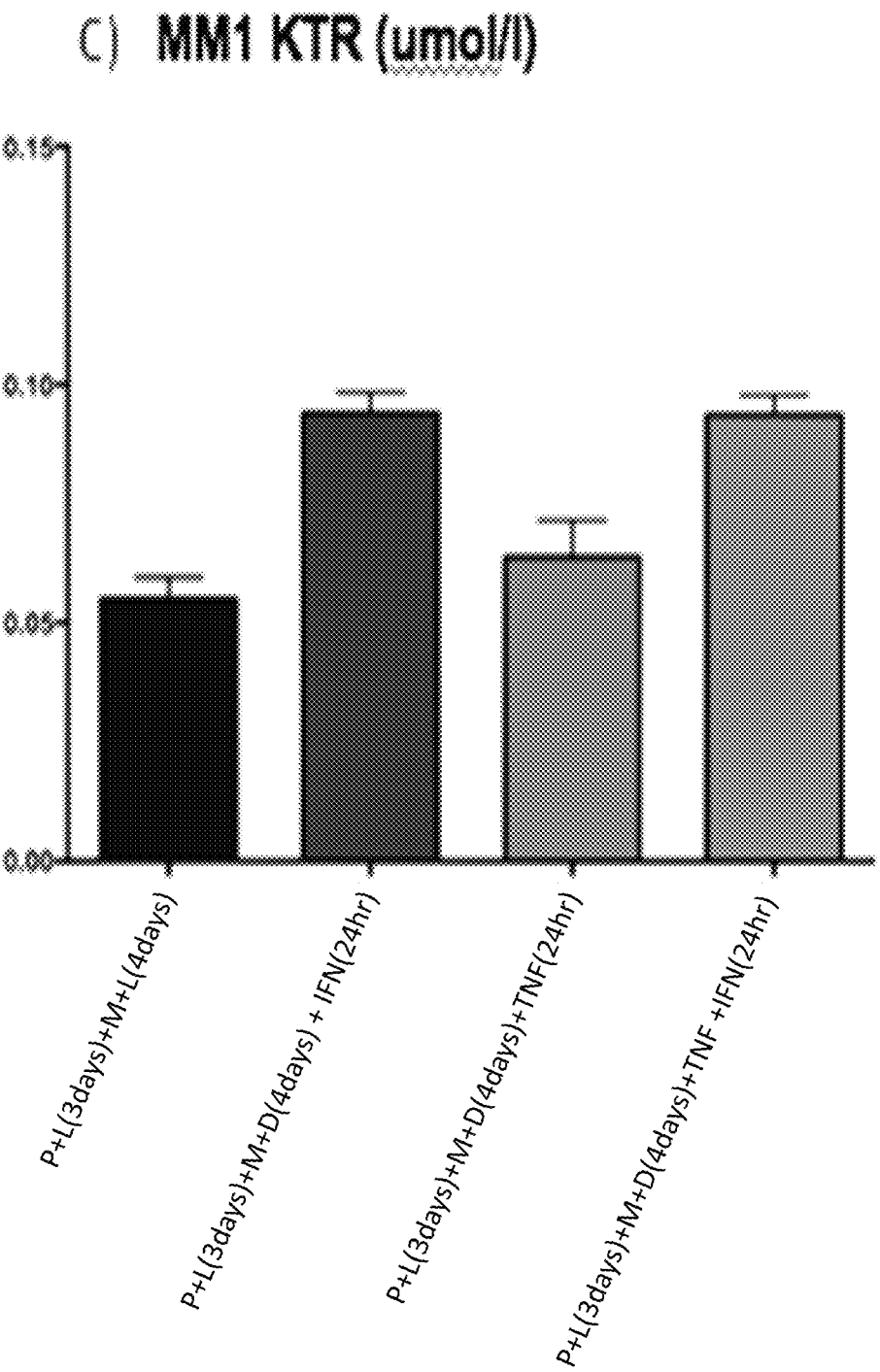

TNF α and IFN γ induce tryptophan catabolism/IDO activity as determined by increase in the kynurenine/tryptophan ratio in cell culture supernatant, in response to TNF alpha and IFN gamma treatment (FIG. 7).

Figure 8:
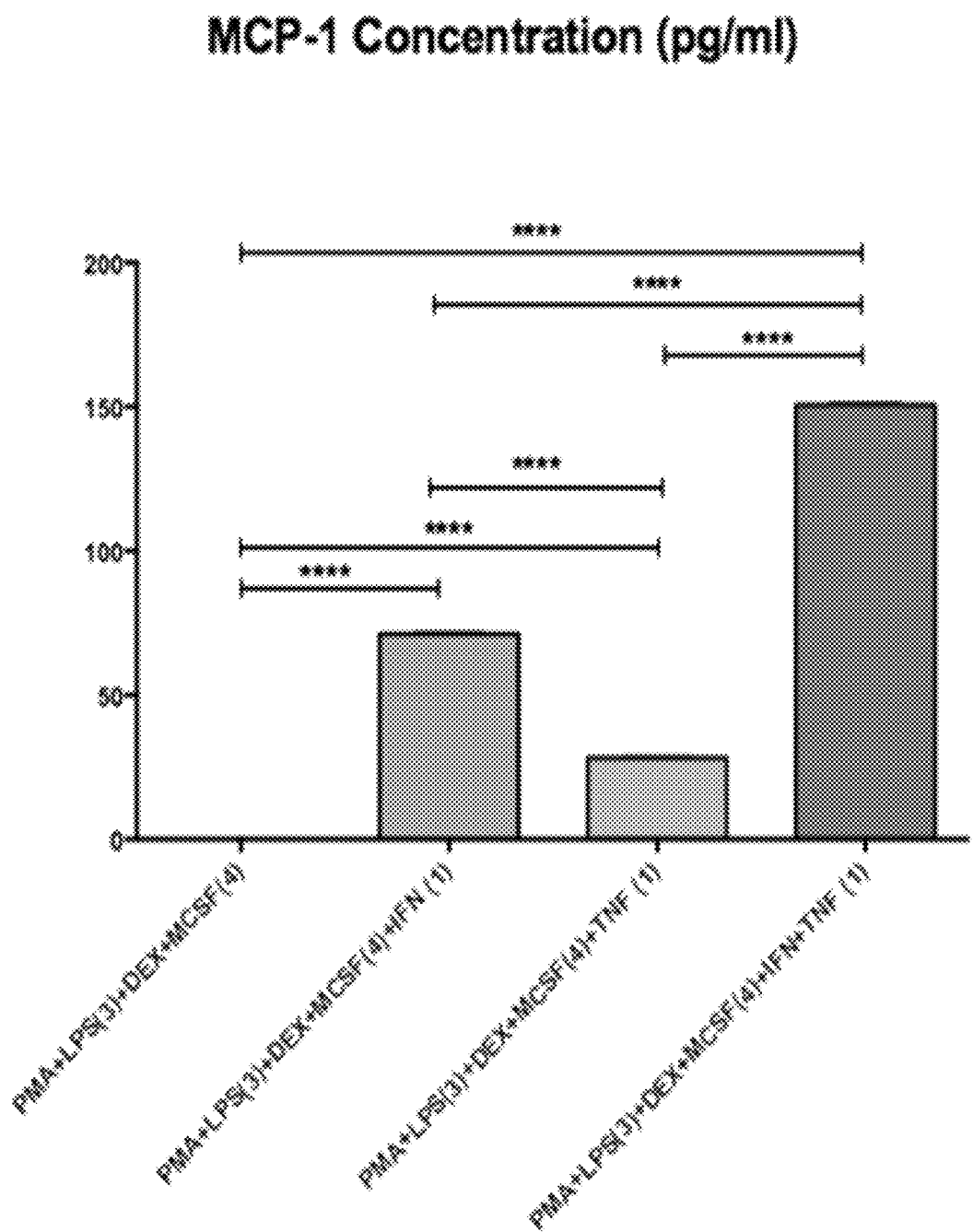
FIG. 8 depicts the results of exemplary experiments demonstrating that IFN and TNF have an effect on increasing the MCP-1 concentration separately, but the combination of IFN and TNF can increase the MCP-1 concentration significantly. (*$p\leq0.05$ and $p\leq0.01$, *$p\leq0.001$, ****$p\leq0.0001$).

Both IFNγ and TNFα each increase MCP-1 and combined show synergistic activation (FIG. 8).

As expanded CD16+ monocytes, kynurenine metabolites, and MCP-1 expression have been implicated in many inflammatory diseases, this culture system provides for a valuable screening tool for drug discovery relevant to many diseases involving inflammation and immune activation.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. An isolated monocyte, wherein the monocyte expresses CD16, CD163, and CD4.

2. The monocyte of claim 1, wherein the monocyte is a MonoMac-1 cell.

3. A culture medium comprising the monocyte of claim 2, phorbol-12-myristate-13-acetate (PMA), and lipopolysaccharide (LPS).

4. A culture medium comprising the monocyte of claim 2, macrophage colony-stimulating factor (MCSF), and dexamethasone (DEX).

5. A culture medium comprising the monocyte of claim 2, TNFα, and IFNγ.

* * * * *